United States Patent [19]

Warriner

[11] Patent Number: Plant 6,316

[45] Date of Patent: Oct. 4, 1988

[54] ROSE PLANT JACARA

[75] Inventor: William A. Warriner, Tustin, Calif.

[73] Assignee: Jackson & Perkins Company, Medford, Oreg.

[21] Appl. No.: 936,007

[22] Filed: Nov. 28, 1986

[51] Int. Cl.[4] ..... A01H 5/00

[52] U.S. Cl. ..... Plt./11

[58] Field of Search ..... Plt./11

*Primary Examiner*—James R. Feyrer

*Attorney, Agent, or Firm*—Majestic, Gallagher, Parsons & Siebert

[57] ABSTRACT

A hybrid tea rose variety having resistance to mildew, reddish rachis and new bark, a distinctive blend of pink and coral red colors in the large flower and dark green foliage borne on an upright, vigorous plant.

1 Drawing Sheet

This present invention relates to a new and distinct variety of rose plant of the hybrid tea class which was originated by crossing an unnamed variety with an unnamed variety.

The primary objective of this breeding was to produce a new rose variety of the hybrid tea class exhibiting constant bloom combined with a vigorous, upright plant habit and a measure of mildew resistance. This objective was substantially achieved along with other desirable improvements as evidenced by the following unique combination of characteristics which are outstanding in the new variety and which distinguish it from its parents as well as from all other varieties of which I am aware:

1. Unusual blend of color;
2. Resistance to powdery mildew;
3. Continuous profuse flowering;
4. Upright, vigorous growth;
5. Glossy, green foliage; and
6. Reddish-colored rachis and new bark.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Unnamed variety.

*Pollen parent.*—Unnamed variety.

Classification:

*Botanical.*—Rosa hybrid.

*Commercial.*—Hybrid tea.

FLOWER

Observations made from specimens grown in a greenhouse at Irvine, Calif. in September and October, 1986.

Blooming habit: Continuous.

Bud:

*Size.*—1½" when petals start to unfurl.

*Form.*—Long, pointed ovoid.

*Color.*—When sepals first divide, already displaying a blend of colors from white (White Group 155D) near the petal base to coral pink to near orange at the petal edges that are exposed to the sun (Red Group 38C to Red Group 43A to C); when half blown, upper side of petals a blend of colors from Red Group 43A to C on the petal edges to a pale pink near the petal base of Red Group 36B to D.; lower side of petals white at the petal base (White Group 155D) to an ever increasing pink at the petal edges (Red Group 36B to D in the middle ⅔'s of the petal) to Red Group 49A at the petal margins.

*Sepals.*—Color: Green Group 138B. Three appendaged sepals normally appendaged. Two unappendaged sepals hairy edged.

*Receptacle.*—Color: Green Group 138B. Shape: Funnel. Size: Small. Surface: Smooth.

*Peduncle.*—Length: Medium to short. Surface: Glandular. Color: Medium green and bronzy. Strength: Stiff, erect.

Open bloom:

*Size.*—Large. Average open size 5".

*Borne.*—Singly to several together.

*Stems.*—Medium, strong.

*Form.*—When first open, high center. Permanence: Flattens slightly and outer petals curl back.

*Petalage.*—Number of petals under normal conditions: 30.

*Color.*—Center of flower: Upper side of petals, a blend of colors dominated by Red Group 43A to C on the petal edges to Red Group 36B to D in the middle to basal part of the petal; reverse side of petals, much lighter colors beginning with White Group 155D at the base and changing to Red Group 36B to D in the middle of the petals to Red Group 49A at the petal margin. Base of petals, White Group 155D. Major color: Dominated by Red Group 43A to C.

*Variegations.*—None.

*Discoloration.*—General tonality at end of first day: None. Third day: Gradual intensification of color until petal drop.

*Fragrance.*—Moderate.

Petals:

*Texture.*—Thick.

*Shape.*—Notched and deltoid.

*Form.*—Tips slightly recurved.

*Arrangement.*—Imbricated.
*Persistence.*—Drop off cleanly.
*Lastingness.*—On the plant, long. As cut flower, long.

Reproductive parts:
*Anthers.*—Medium. Color: Reddish brown. Arrangement: Regular around styles.
*Filaments.*—Color: Yellow.
*Pollen.*—Gold yellow.
*Styles.*—Color: Reddish.
*Stigmas.*—Color: Greenish white.

PLANT

Form: Bush.
Growth: Vigorous.
Foliage: Number of leaflets on normal mid-stem leaves: 5 to 7.
*Size.*—Large.
*Quantity.*—Abundant.
*Color.*—New foliage: Red. Old foliage: Dark green (Green Group 139A).

Leaflets:
*Shape.*—Oval pointed.
*Texture.*—Leathery and glossy.
*Edge.*—Serrated.

*Serration.*—Single, medium.
*Petiole.*—Rachis: Color: Reddish. Underside: Smooth, with prickles.
*Stipules.*—Medium, bearded.
*Disease resistance.*—Resistant to mildew, under normal growing conditions at Irvine, Calif.

Wood:
*New wood.*—Color: Reddish. Bark: Smooth.
*Old wood.*—Color: Green. Bark: Smooth.

Prickles:
*Quantity.*—On main canes from base: Ordinary. On laterals from main canes: Ordinary.
*Form.*—Hooked downward.
*Color when young.*—Red.

Small prickles:
*Quantity.*—On main stalks, none. On laterals, none.

I claim:

1. A new and distinct variety of rose plant of the hybrid tea class, substantially as herein shown and described, characterized particularly as to novelty by the unique combination of its resistance to mildew, its reddish rachis and new bark, its distinctive blend of pink and coral red colors in the large flower and its dark green foliage borne on an upright, vigorous plant.

* * * * *

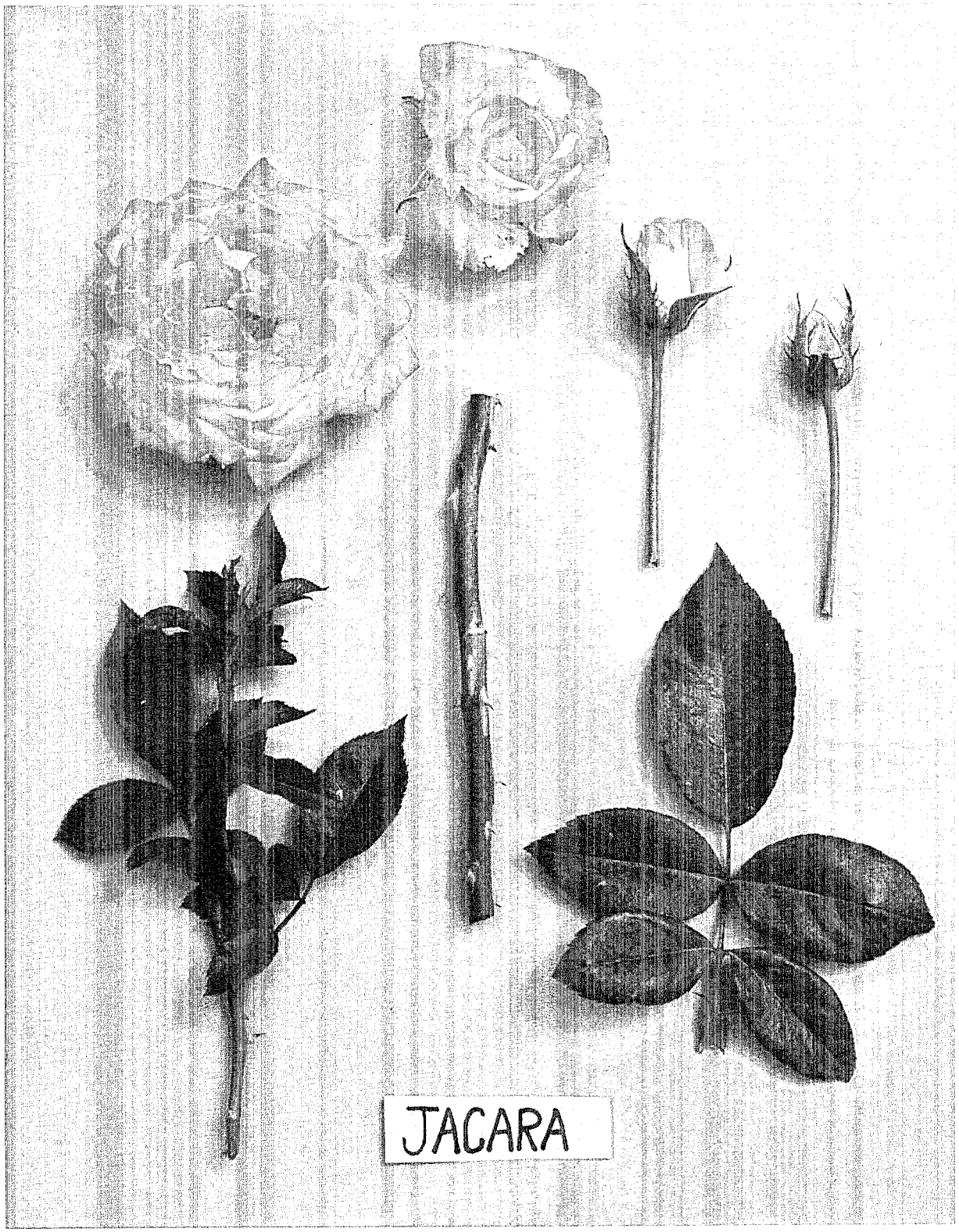
JACARA